(12) United States Patent
Rigoletto, Jr. et al.

(10) Patent No.: US 6,451,299 B1
(45) Date of Patent: Sep. 17, 2002

(54) SYNERGISTIC EFFECT ON VISCOSITY BETWEEN ASSOCIATIVE POLYMERS

(75) Inventors: Raymond Rigoletto, Jr., Denville; Joseph Albanese, Belle Mead, both of NJ (US)

(73) Assignee: ISP Investments Inc., Wilmington, DE (US)

(*) Notice: Subject to any disclaimer, the term of this patent is extended or adjusted under 35 U.S.C. 154(b) by 0 days.

(21) Appl. No.: 09/557,623

(22) Filed: Apr. 25, 2000

(51) Int. Cl.[7] .............. A61K 7/06; A61K 7/11
(52) U.S. Cl. ........... 424/70.16; 424/70.1; 424/70.11; 424/70.15; 424/401
(58) Field of Search ............... 424/70.1, 70.11, 424/401, 70.15, 70.16

(56) References Cited

U.S. PATENT DOCUMENTS

| 5,656,257 | A | * | 8/1997 | Fealy et al. |
| 5,900,229 | A | * | 5/1999 | Dupuis |
| 5,965,115 | A | * | 10/1999 | Bolich, Jr. et al. |
| 5,968,493 | A | * | 10/1999 | Dornoff |

* cited by examiner

Primary Examiner—Thurman K. Page
Assistant Examiner—Todd D Ware
(74) Attorney, Agent, or Firm—Walter Katz; William J. Davis; Marilyn J. Maue

(57) ABSTRACT

A personal care composition having synergistic rheological properties and aesthetic and functional gel at low solids blends comprising a blend of (a) a terpolymer of polyvinylpyrrolidone, acrylic acid and laurylmethacrylate; and (b) a copolymer of acrylates and steareth-20 methacrylate.

10 Claims, 10 Drawing Sheets

Figure 1:
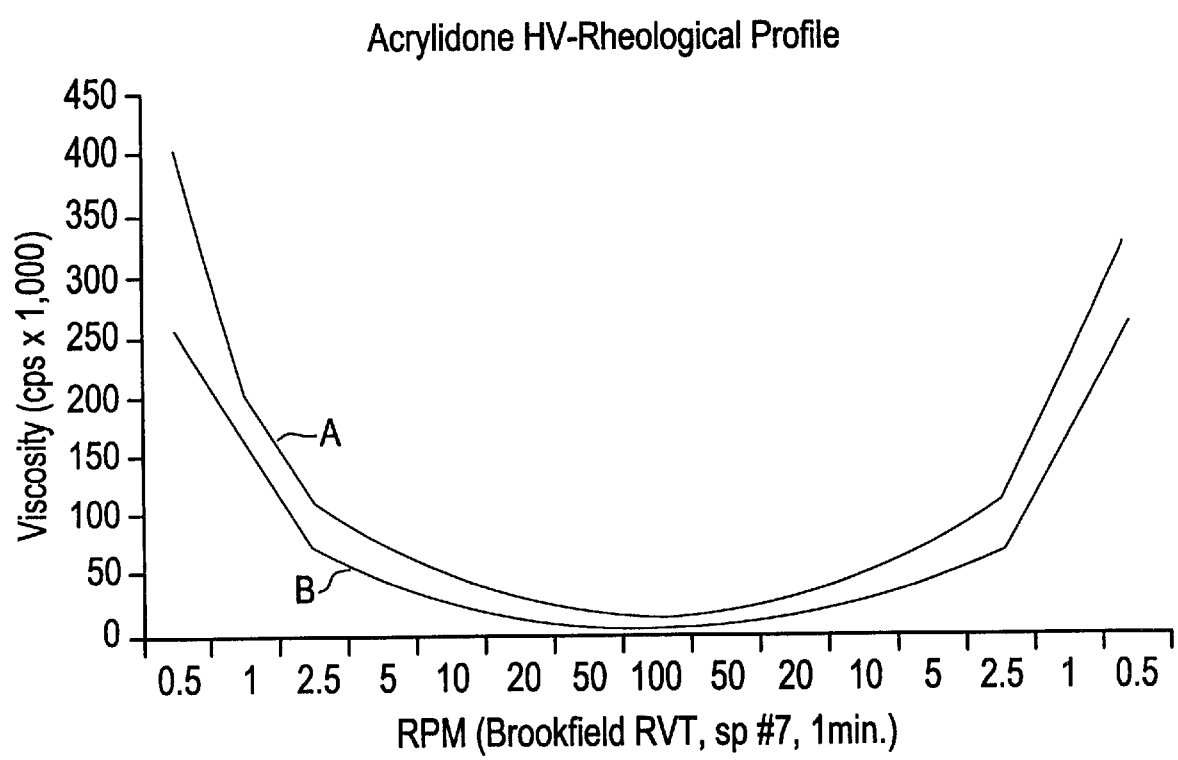

(A) 0.50% Terpolymer, 0.50% Copolymer
(B) 0.50% Terpolymer, 0.50% Carbomer (A) 0.50% Terpolymer, 0.50% Copolymer
(B) 0.50% Terpolymer, 0.50% Carbomer Interactive effect of Terpolymer and Copolymer

SYNERGISTIC EFFECT ON VISCOSITY BETWEEN ASSOCIATIVE POLYMERS

BACKGROUND OF THE INVENTION

1. Field of the Invention

This invention relates to personal care products, and, more particularly, to a hair gel composition which is a blend of two polymers which together exhibit a synergistic rheological and viscosity effects on the composition, as well as providing advantageous fixative, curl retention, suspending and clarity properties.

2. Description of the Prior Art

Today's consumer has a wide range of products available for hair care. This includes many product forms designed for styling such as mousses, hair sprays, setting lotions and hair gels. The popularity of hair gels makes them a significant portion of the hair care market. Essential to the acceptance of styling gels by consumers are aesthetics and performance. Attributes of aesthetic properties are clarity, color, odor, appearance, rheological behavior, and easy dispersing from a tube or jar. Performance attributes include high humidity curl retention, and hair characteristic qualities such as easy application, non-tacky feel, quick drying, no residue or flaking, increased hair body and volume, good gloss or shine, and in most cases not too excessively stiff. Another important consideration is easy removal by shampooing. So one can see that many factors go into play in the formulation of an acceptable and functional hair styling product.

A basic styling gel contains a good diluent. Most typically, the diluent consists of deionized water but it also may contain an alcohol, such as ethanol, although regulatory requirements have set an upper limit at 6.0% VOC for such products. The next most common ingredients in styling gels are the hair fixative polymers and the gelling or thickening system. In many cases a neutralizer also is required for the functionality of the gellant. Auxiliary ingredients normally include preservatives, UV absorbers to protect the product or UV sunscreens to protect the hair from sun damage, chelating agent, fragrance, color, and solubilizers such as nonionic surfactants. If the gel is to also function as a conditioner such ingredients as protein derivatives, silicone derivatives, or quaternary ammonium compounds must be added as well. A typical hair gel formulation is given in Table 1 below.

TABLE 1

| Ingredient | % by Weight |
|---|---|
| Water | q.s. to 100% |
| SD Alcohol 40 | 0–6% |
| Polymer | 1–5% |
| Gelling Agent/Thickener | 0.25–1.0% |
| Neutralizing Base | 0.50–1.5% |
| Nonionic Surfactant | 0.5–2% |
| Fragrance | 0.1–0.4% |
| Preservative | 0–1% |
| Ultraviolet Screen | <0.1% |
| Chelating Agent | <0.1% |
| Miscellaneous | 0–1.0% |

SUMMARY OF THE INVENTION

What is described herein is a composition having a unique rheological and viscosity synergy between blends of the defined terpolymer and copolymer. These associative polymers have hydrophobic moieties along their hydrophilic backbone which form inter- and intra-molecular linkages. This network increases viscosity above that due to just the mechanism of chain entanglement alone. The theoretical mechanism of action is that both associative polymers form a network with themselves to promote a unique viscosity enhancement in personal care products such as hair gels. This synergistic effect allows for low levels of the polymers in hair care compositions without affecting other attributes of the physical properties of the product or its performance on the hair. Although hair care gels are emphasized in this invention, efficacious gels using the synergistic composition of the invention can be produced also for skin care, such as eye gel products.

DESCRIPTION OF THE INVENTION

Acrylidones are a line of products that are based on the copolymerization of vinylpyrrolidone and acrylic acid. One derivative of such chemistry is a terpolymer of a PVP/acrylate copolymer which is hydrophobically modified with $C_{12}$ groups, i.e. a polyvinylpyrrolidone/acrylic acid/lauryl methacrylate terpolymer (Formula 1), (referred to herein after as "TERPOLYMER"). This terpolymer is available in a wide range of monomer ratios typically 20–90 wt. % VP, 1–55 wt. % AA and 1–25 wt. % LM. Preferably the terpolymer has about 50–75% VP, 15–30% M and 5–15% LM. The acrylic acid portion can be neutralized with an alkaline earth base such as sodium hydroxide or an organic amine such as aminomethylpropanol. The degree of neutralization, based on the acrylic acid portion of the terpolymer, can range from 10 to 100%.

FORMULA 1

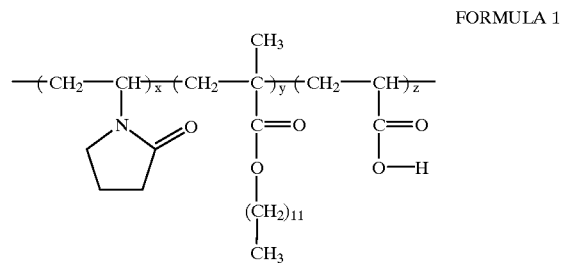

Thickeners most typically used in hair styling gels are Carbomers, cellulose derivatives such as hydroxyethyl cellulose HEC, PVM/MA decadiene crosspolymer, and acrylates/steareth-20 methacrylate copolymer.

Aculyn® 28 from Rohm & Haas is an Acrylates/Beheneth-25 Methacrylate Copolymer (referred to hereinafter as "COPOLYMER"), is a thickener/stabilizer having the structure shown in (Formula 2). It is supplied as a milky white, 20% solids aqueous solution at pH 3.0+/−0.5. Thickening is immediate when neutralized with a suitable base. It also is a hydrophobically modified alkali soluble emulsion (HASE) and it thickens by two distinct mechanisms: (1) charge induced polyelectrolytic chain expansion and (2) association of alkyl groups.

FORMULA 2

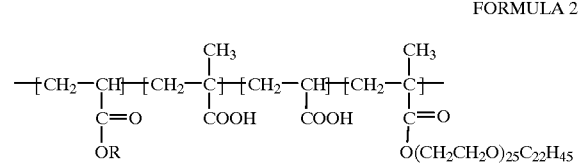

The invention will now be described with reference to the following examples.

EXAMPLE 1

A typical hair gel composition of the invention is shown in Table 2 below. This composition is a clear, thick gel that possesses excellent performance on hair especially for high humidity curl retention. In this composition, there is a unique synergistic viscosity effect for the combination of Terpolymer and Copolymer as described in detail hereinafter. This increased viscosity effect is present without affecting the rheological properties of the gel; specifically, the product is still pseudoplastic and spreads very well during application. Another feature of this formulation is its advantageous performance is achieved at a very low level of about 1.0% total solids.

TABLE 2

Hair Gel Composition of Invention

| Ingredients: | Wt. % |
|---|---|
| D.I. Water | 96.22 |
| Terpolymer | 0.50 |
| PVP/Acrylic Acid/Lauryl Methacrylate | |
| AMP-95 | 0.05 |
| Copolymer | 2.40 |
| Acrylates/Beheneth-25 Methacrylate Copolymer | |
| AMP-95 | 0.23 |
| Na$_2$EDTA (sodium ethylenediamine tetraacetic acid) | 0.10 |
| Preservative | 0.50 |
| Total | 100.00 |

The physical properties of such an invention formulation is given in Table 3 below.

TABLE 3

| | |
|---|---|
| Viscosity cps | 96 M, (TE, 5, RVT) |
| Terpolymer and Copolymer Solids | 0.5 + 0.5 = 1.0% |
| pH | 6.74 |
| Color | Water white |
| Odor | Very slight |
| Appearance | Clear |

Procedure to Manufacture

1. Disperse Terpolymer into room temperature water with propeller agitation. Mix until well dispersed; about 20 minutes.
2. Add first addition of AMP to the batch; batch will thicken slightly and become less opaque.
3. Add Copolymer and mix until uniform.
4. Change propeller to paddle blade.
5. Resume agitation after 10 minutes to allow the batch to deaerate.
6. Add the second addition of AMP very slowly to the batch under moderate to slow agitation (about 100 rpm). Product will then start to thicken. Mix until uniform.
7. Dissolve Na$_2$EDTA and preservative. Adjust pH with AMP to obtain a pH of 6.70±0.10.

Table 4 below are invention examples and comparative data to establish the synergistic action of blends of Terpolymer and Copolymer in the hair gel of Table 2 on increasing the viscosity of the gel over similar formulations with only the individual components.

TABLE 4

| | | | | Viscosity (cps) |
|---|---|---|---|---|
| Invention Examples | | | | |
| Ex. No. | Terpolymer (% Solids) | + | Copolymer (% Solids) | |
| 1 | 0.5 | | 0.5 | 96,000 |
| 2 | 1.0 | | 0.5 | 117,000 |
| 3 | 2 | | 0.5 | 180,000 |
| 4 | 3 | | 0.5 | 298,000 |
| 5* | 0.5 | | 0.5 | 240,000 |
| COMPARATIVE EXAMPLES | | | | |
| | Fixative (% Solids) | + | Gellant (% Solids) | |
| A | 2 Terpolymer | | None | 275 |
| B | 0.5 Terpolymer | + | 1.2 HEC | 26,000 |
| C | 0.5 Terpolymer | + | 0.5 Carbomer | 67,000 |
| D | 1.0 Terpolymer | + | 0.5 Carbomer | 78,000 |
| E | 3 PVPNA | + | 0.5 Copolymer | 1,050 |
| F | None | | 0.5 Copolymer | 1,200 |

*(+ Polysorbate-20 + Oleth-20)

As can be clearly seen in Table 4, there is a direct relationship on viscosity with the level of Terpolymer when the Copolymer is used at a constant level of 0.50%. The data from these additional formulas provide the following conclusions:

Terpolymer by itself is not a primary viscosifier.

Terpolymer in other gellants such as HEC, and Carbomer 940 have a lower viscosity response than in systems with Copolymer.

Copolmer in other fixatives that are non-associative, such as PVP/VA, have poor viscosity effects.

This viscosity enhancement of the composition of the invention is achieved without affecting the Theological profile of the gel. Ideally the gel needs to possess shear thinning properties so that it can be spread through the hair and coat the individual hair fibers; that is, the rheology of the gel -needs to be pseudoplastic. As can be seen in FIG. 1, both the formula based on our present invention and that based on Carbopol have the same pseudoplastic rheology.

An experimental design was performed to explore this viscosity synergy in more detail. By analysis of the resultant viscosity data it was concluded that the viscosity effect is truly synergistic. This analysis is illustrated with leverage plots that indicate statistical significance of effects, and a phase or ternary diagram.

The actual formulas made in the design with the resultant viscosity data are presented in Table 5. These data columns were used in the analysis. The predicted formula for viscosity is a result of multiple regression.

The rheology of such gels makes them suitable for dispensing either as rigid stiff gels that can be dispensed from jars or tubes or as easily thinned gels that can be dispensed from a pump spray package.

TABLE 5

| Terpoly-Mer | Copoly-mer | Other | Viscosity (cps) | % Terpolymer | % Copolymer | Total | Pred Formula Viscosity |
|---|---|---|---|---|---|---|---|
| 0.01 | 0.005 | 0.985 | 127000 | 0.666667 | 0.333333 | 0.015 | 119579.9 |
| 0.01 | 0.001 | 0.989 | 130 | 0.909091 | 0.090909 | 0.011 | 20453.26 |
| 0.005 | 0.005 | 0.99 | 101000 | 0.5 | 0.5 | 0.01 | 79312.25 |
| 0.005 | 0.001 | 0.994 | 60 | 0.833333 | 0.166667 | 0.006 | −4726.75 |
| 0.005 | 0.003 | 0.992 | 25000 | 0.625 | 0.375 | 0.008 | 37292.75 |
| 0.01 | 0.003 | 0.987 | 32000 | 0.769231 | 0.230769 | 0.013 | 70016.57 |
| 0.0075 | 0.001 | 0.9915 | 100 | 0.882353 | 0.117647 | 0.0085 | 7863.256 |
| 0.0075 | 0.005 | 0.9875 | 101000 | 0.6 | 0.4 | 0.0125 | 99446.06 |
| 0.02 | 0.005 | 0.975 | 180000 | 0.8 | 0.2 | 0.025 | 200115.1 |
| 0.03 | 0.005 | 0.965 | 298000 | 0.857143 | 0.142857 | 0.035 | 280650.3 |
| 0.005 | 0 | 0.995 | 24 | 1 | 0 | 0.005 | −25736.5 |
| 0.0075 | 0 | 0.9925 | 32 | 1 | 0 | 0.0075 | −15032.4 |
| 0.01 | 0 | 0.99 | 48 | 1 | 0 | 0.01 | −4328.39 |
| 0.02 | 0 | 0.98 | 7000 | 1 | 0 | 0.02 | 38487.85 |
| 0.03 | 0 | 0.97 | 105000 | 1 | 0 | 0.03 | 81304.08 |
| 0 | 0.001 | 0.999 | 12 | 0 | 1 | 0.001 | −29906.8 |
| 0 | 0.003 | 0.997 | 32 | 0 | 1 | 0.003 | 4568.934 |
| 0 | 0.005 | 0.995 | 1200 | 0 | 1 | 0.005 | 39044.64 |
| 0 | 0.01 | 0.99 | 146000 | 0 | 1 | 0.01 | 125233.9 |

Figure 2:
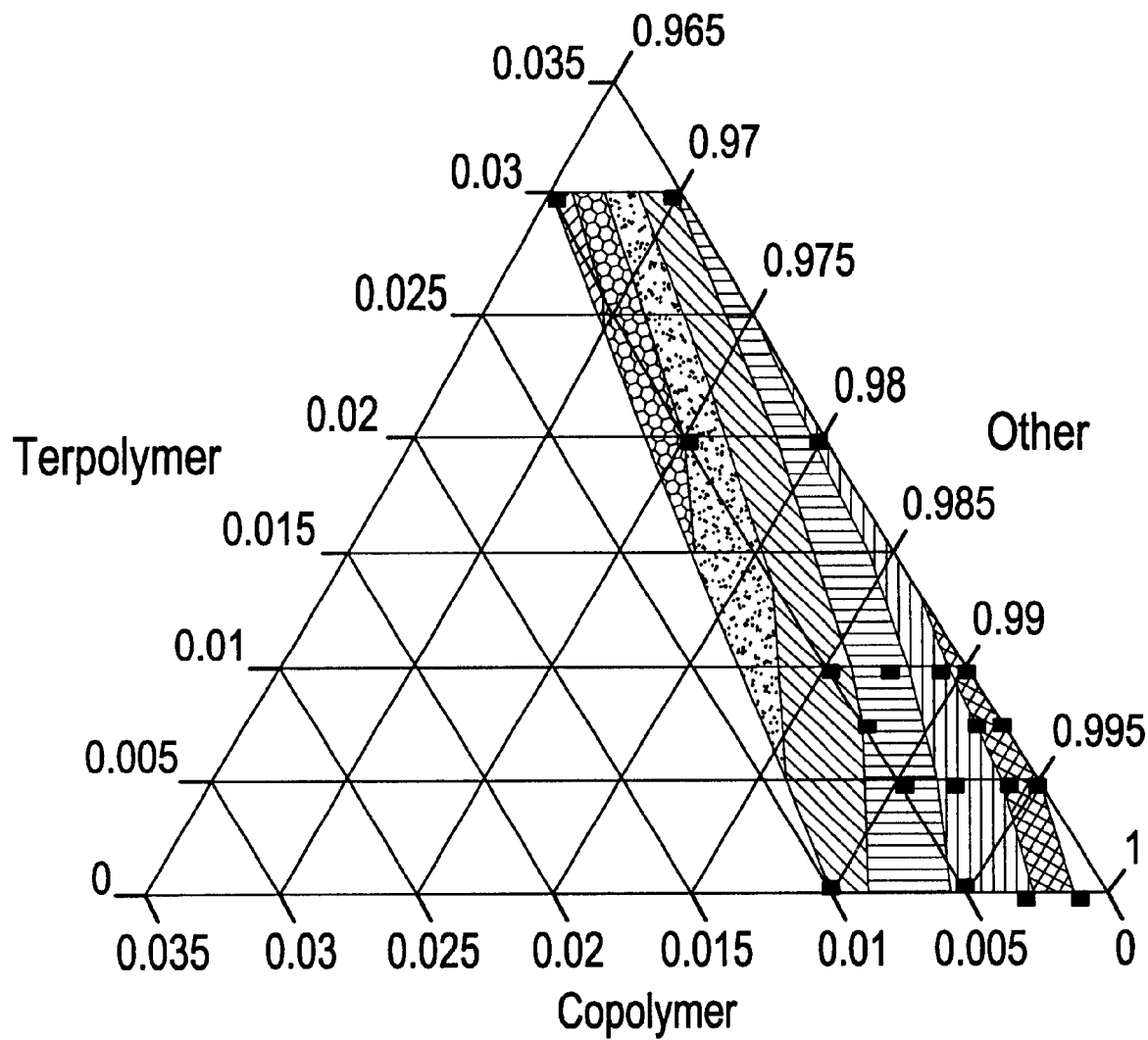

Viscosity performance is indicated in the ternary diagram, FIG. 2. This illustrates that as the level of the polymers is increased the viscosity increases. Synergy is confirmed in further analysis of the data.

Data Analysis for ternary phase diagram

TABLE 6

Response: Viscosity
Summary of Fit

| Rsquare | 0.931635 |
|---|---|
| Rsquare Adj | 0.917961 |
| Root Mean Square Error | 23899.63 |
| Mean of Response | 59138.84 |
| Observations (or Sum Wgts) | 19 |

TABLE 7

Parameter Estimates

| Term | Estimate | Std Error | t Ratio | Prob > |t| |
|---|---|---|---|---|
| Intercept | −47144.62 | 12125.55 | −3.89 | 0.0015 |
| Terpolymer | 4281623.3 | 899013.6 | 4.76 | 0.0003 |
| Copolymer | 17237851 | 2684709 | 6.42 | <.0001 |
| Blend | 754380024 | 2.2173e8 | 3.40 | 0.0039 |

TABLE 8

Effect Test

| Source | Nparm | DF | Sum of Squares | F Ratio | Prob > F |
|---|---|---|---|---|---|
| Terpolymer | 1 | 1 | 1.29559e10 | 22.6822 | 0.0003 |
| Copolymer | 1 | 1 | 2.3548e+10 | 41.2261 | <.0001 |
| Blend | 1 | 1 | 6611910076 | 11.5756 | 0.0039 |

Interpretation of Leverage Plots

Figure 3:
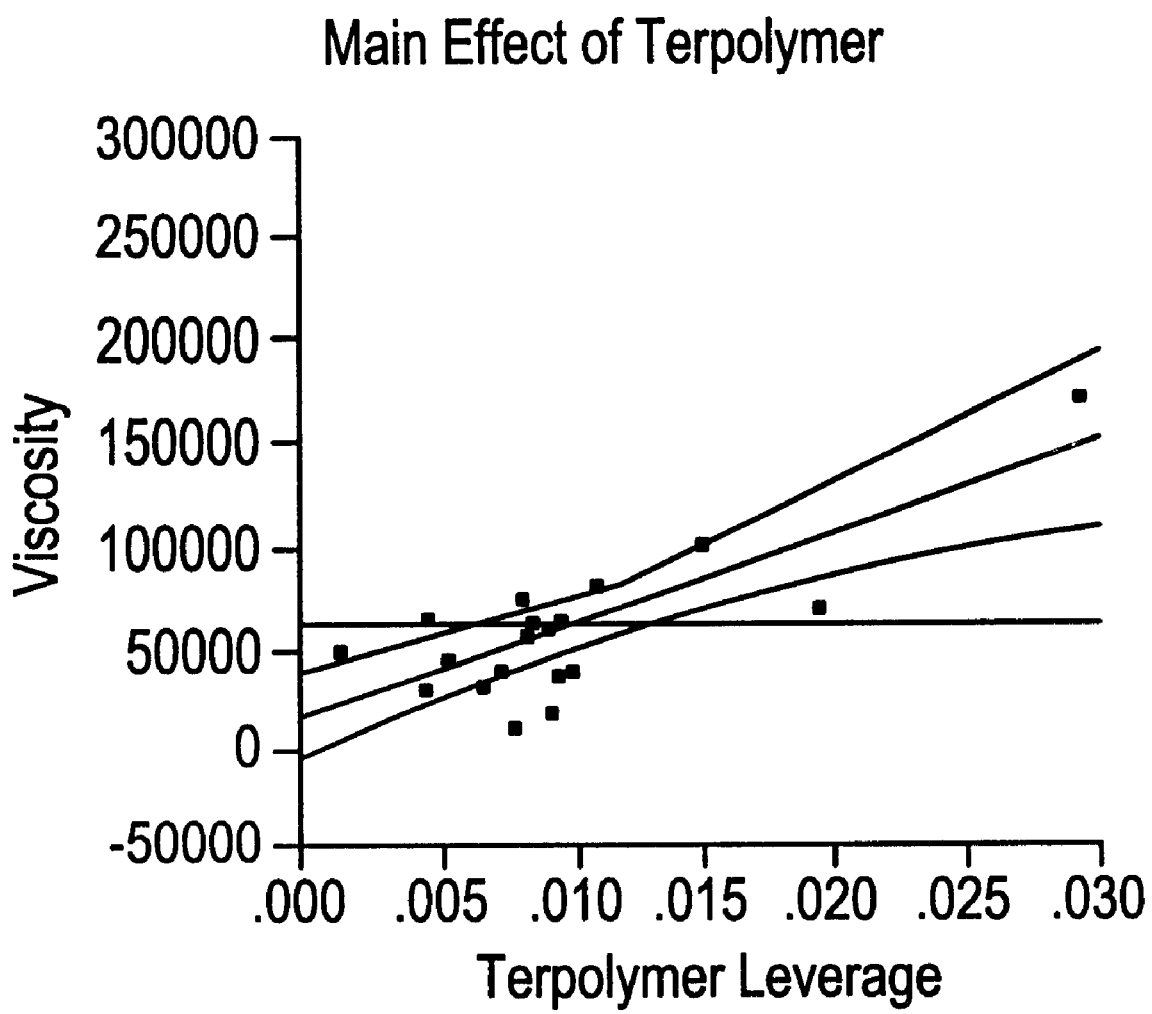
Figure 4:
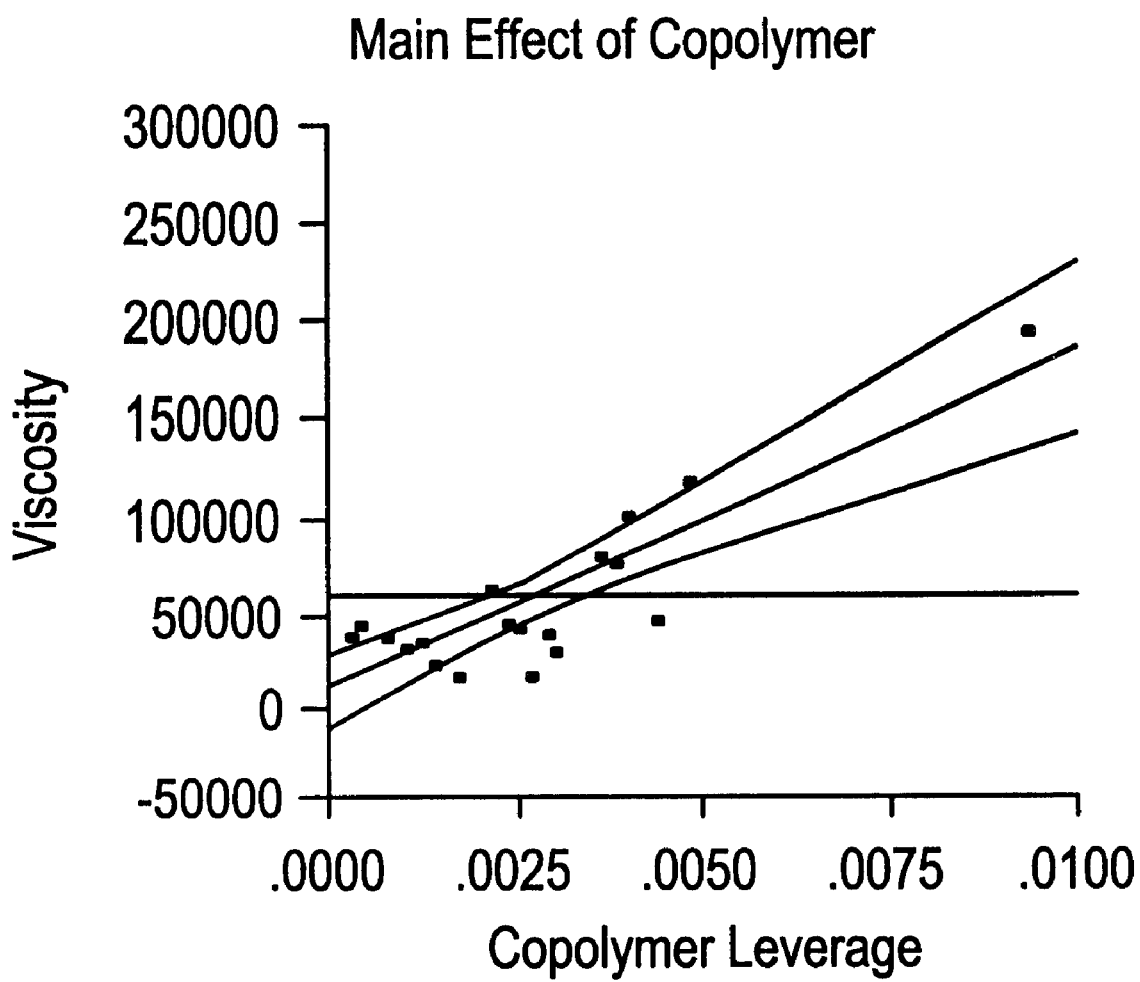
Figure 5:
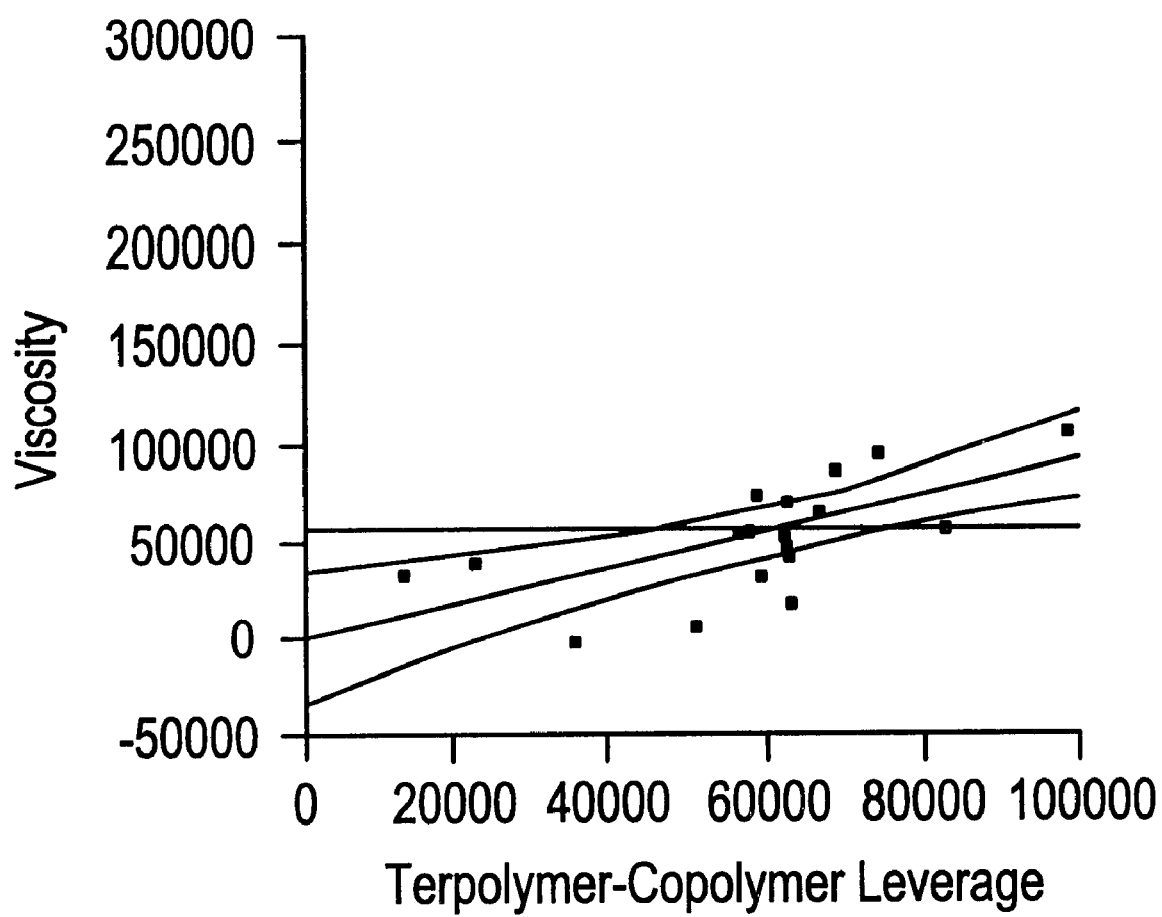

The leverage plots indicated the particular significance of the effect of a variable on a response. They are used for individual variables to determine main effects as well as the significance of interactive effects between variables such as in this case where there is synergistic effects between two polymers. Basically when the line of best fit and its corresponding 95% confidence interval curves cross the horizontal line it can be concluded that the effect of the one variable or interaction of multiple variables has a significant effect. If the outer 95% confidence lines of the centerline of best fit encompass the horizontal line it can be concluded that the variables are of no effect in a particular response. FIGS. 3, 4, and 5 illustrate the leverage plots for the main and interactive effects of Terpolymer and Copolymer.

The leverage plots show that blends of Terpolymer and Copolymer have a major effect in increasing viscosity in hair-gel systems. The unique finding is that the combination of leverage plot shows that there is a statistically significant interaction effect on viscosity when the polymers are used together; that is, they work synergistically with each other to increase viscosity over individual components. Demonstration of $2^{nd}$ order (a.k.a. quadratic effects), or higher order polynomial effects are another critical proof of its synergistic interaction.

Viscosity Synergy Between Terpolymer and Copolymer at a Total of 1% Active

Figure 6:
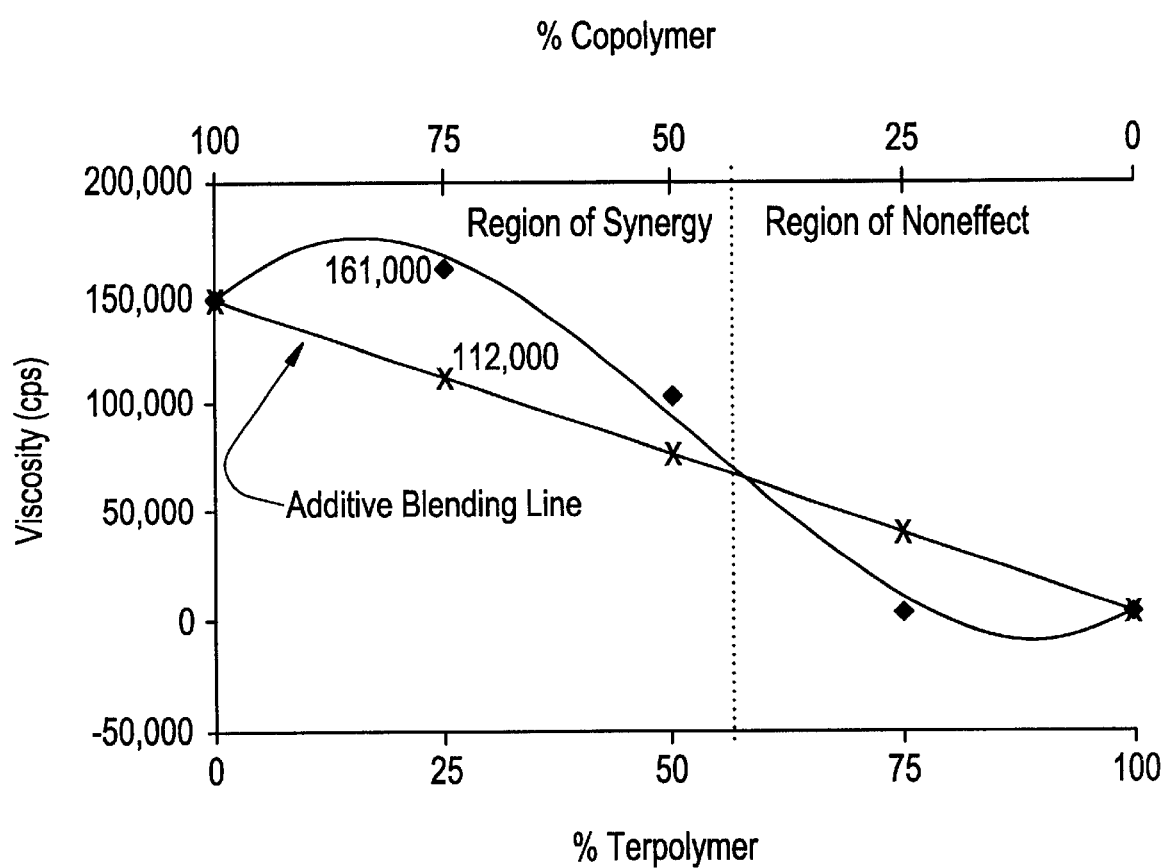

When the total percent solids was held constant at 1.0%, effect produced on viscosity by the PVP/AA/LM to Copolymer interaction can be clearly demonstrated by the following graph as illustrated in FIG. 6. The line marked "Additive Blending Line" is what is expected if the two polymers just had an additive effect on viscosity, e.g. a 50:50 mixture of the two polymer =Visc. A+Visc. B/2 which is in this case 78,000cps. The higher order polynomial curve represents a line of best fit through actual experimental data points. A 75:25 Copolymer:Terpolymer ratio for producing the most dramatic benefit at low actives. The actual observed viscosity (161,000 cps) at this point was 43% higher than the calculated value for the more expected additive nature of the combination.

Viscosity Synergy Between Tergolymer and Copolymer at Variable % Solids

Figure 7:
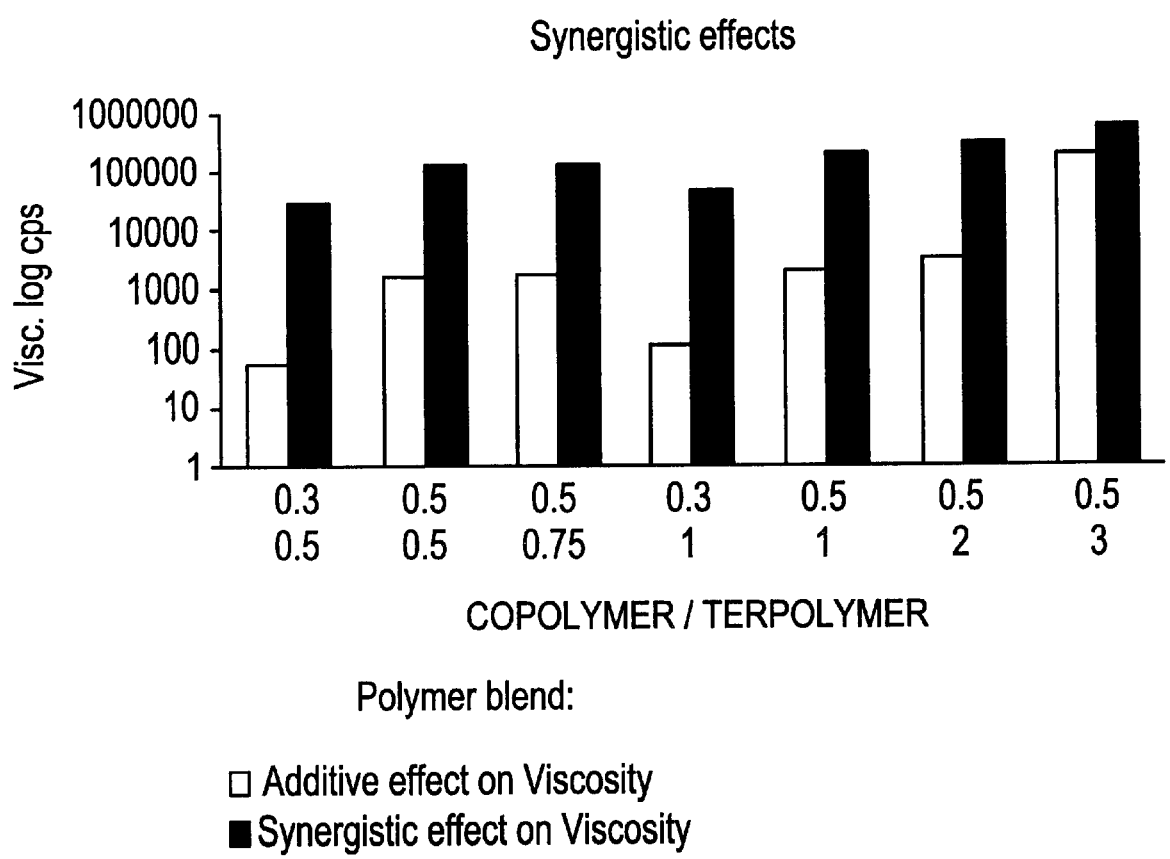

In Table 9 the Additive Effect On Viscosity is what would be expected if the resultant viscosities of the individual components are merely added together. The actual observed experimental results for the combination of polymers is shown by the data under Synergistic Effect On Viscosity. As can be clearly seen in the subsequent bar graph, FIG. 7, the combination of Terpolymer and Copolymer at various solids levels it is observed that viscosity effects are much higher than merely an additive effect.

TABLE 9

| Terpolymer | Copolymer | Additive Effect on Viscosity | Synergistic Effect on Viscosity |
|---|---|---|---|
| 0.5 | 0.3 | 56 | 25000 |
| 0.5 | 0.5 | 1224 | 101000 |
| 0.75 | 0.5 | 1232 | 101000 |
| 1 | 0.3 | 80 | 32000 |
| 1 | 0.5 | 1248 | 127000 |
| 2 | 0.5 | 1900 | 180000 |
| 3 | 0.5 | 106200 | 298000 |

Synergistic Effects of Composition of Invention in Surfactant Systems

Another unexpected outcome was observed in surfactant systems. Based on the positive viscosity response of Terpolymer and Copolymer in gel systems, the polymers were added to a basic anionic shampoo system. The same synergistic behavior was observed. The two polymers at 0.5% each caused the viscosity of the resultant shampoo system became so high as to become unmixable. Lower levels provide a more acceptable viscosity.

Accordingly, many surfactant systems that ordinarily are hard to thicken can be treated by the composition of the invention, including alpha olefin sulfanates, acyl glutamates, and alkyl polyglucosides wherein the associative nature of the polymers are the thickening mechanism instead of containing a polymer or oligamer that has to interact with the surfactant. That is, the thickening system is independent of the surfactant system and can show more flexibility in its thickening with a wider variety of ingredients.

Clarity

Figure 8:
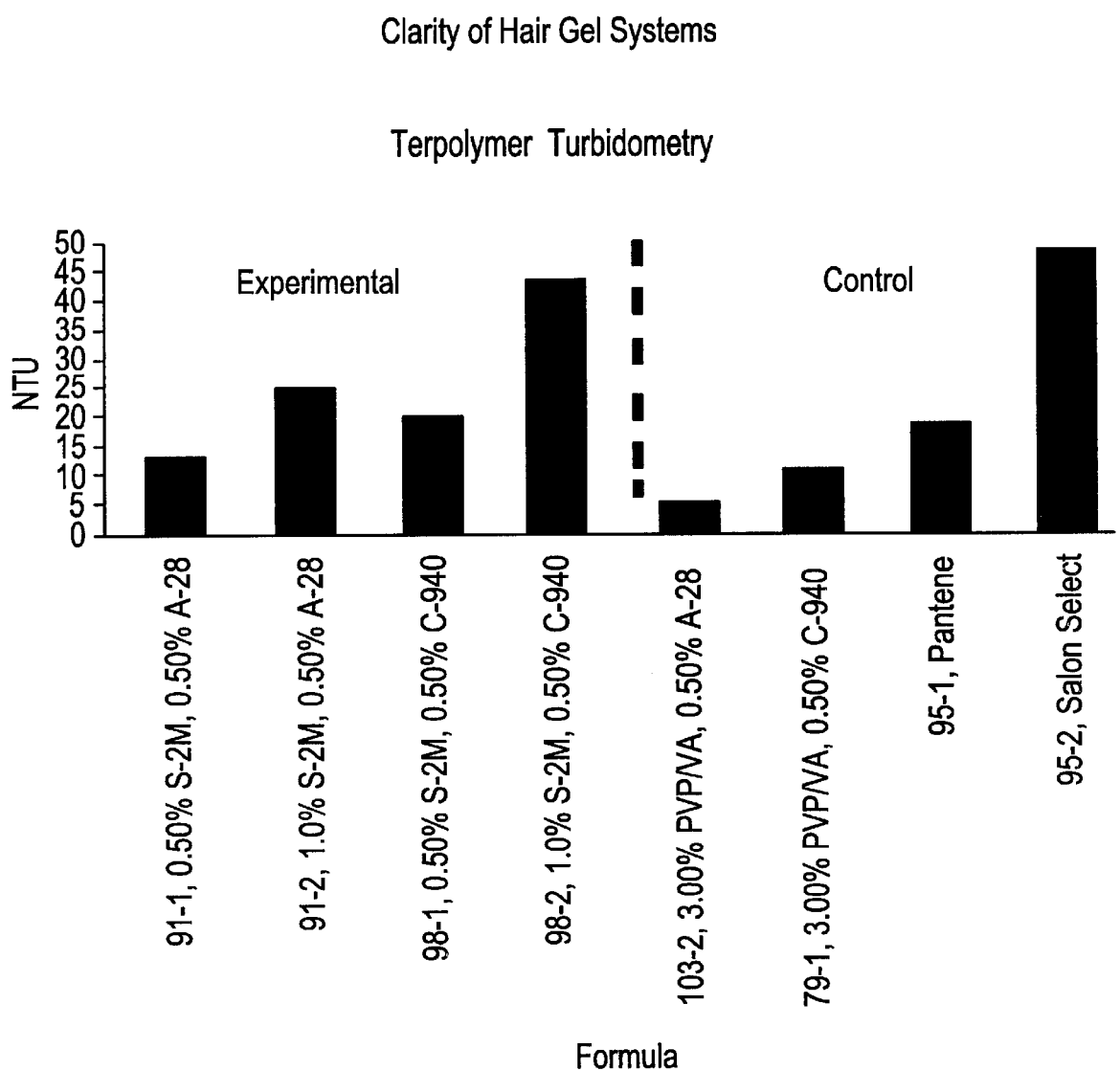

Other benefits besides the synergistic effect on viscosity between the composition of Terpolymer and Copolymer have been observed. One benefit is that clear gels are produced. This characteristic is illustrated in FIG. 8 which shows that 0.5 and 1% Terpolymer are clearer in Copolymer than that obtained in Carbopol 940.

Clarity of Films

Films of these gels were cast with the use of a 0.003" draw down blade on a clean glass plate. It was observed that dry films containing a combination of Terpolymer and Copolymer each are crystal clear. This result is in sharp contrast to a gel using Carbomer 940 at 0.5% and PVP/VA at 3.0% where the resultant dry film was observed to be very hazy.

Goniophotometry

Hair was treated with invention formula (0.5% Terpolymer and 0.5% Copolymer and composition formulas (0.5% Carbomer 940 and 3.0% PVP/VA) and measured goniophotometrically to determine differences in shine. The invention formula had a higher specular reflectance than standard showing that the invention formula imparted more shine to the hair.

High Humidity Curl Retention

Figure 9:
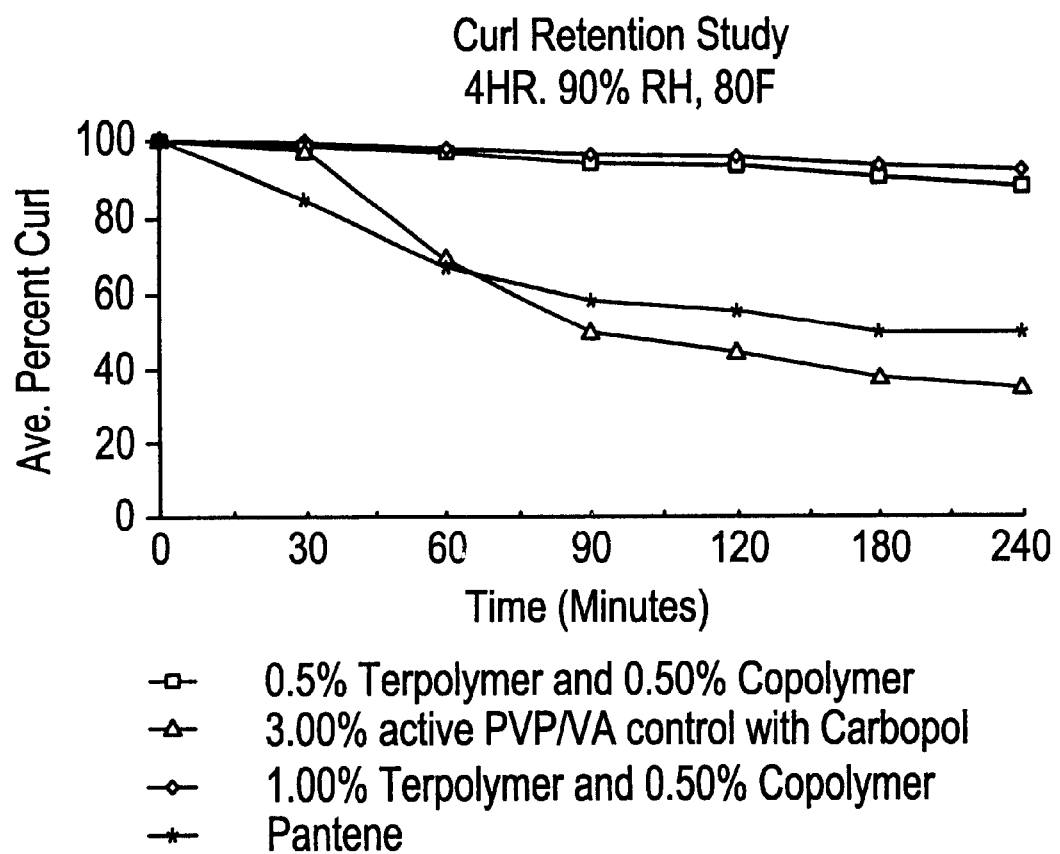
Figure 10:
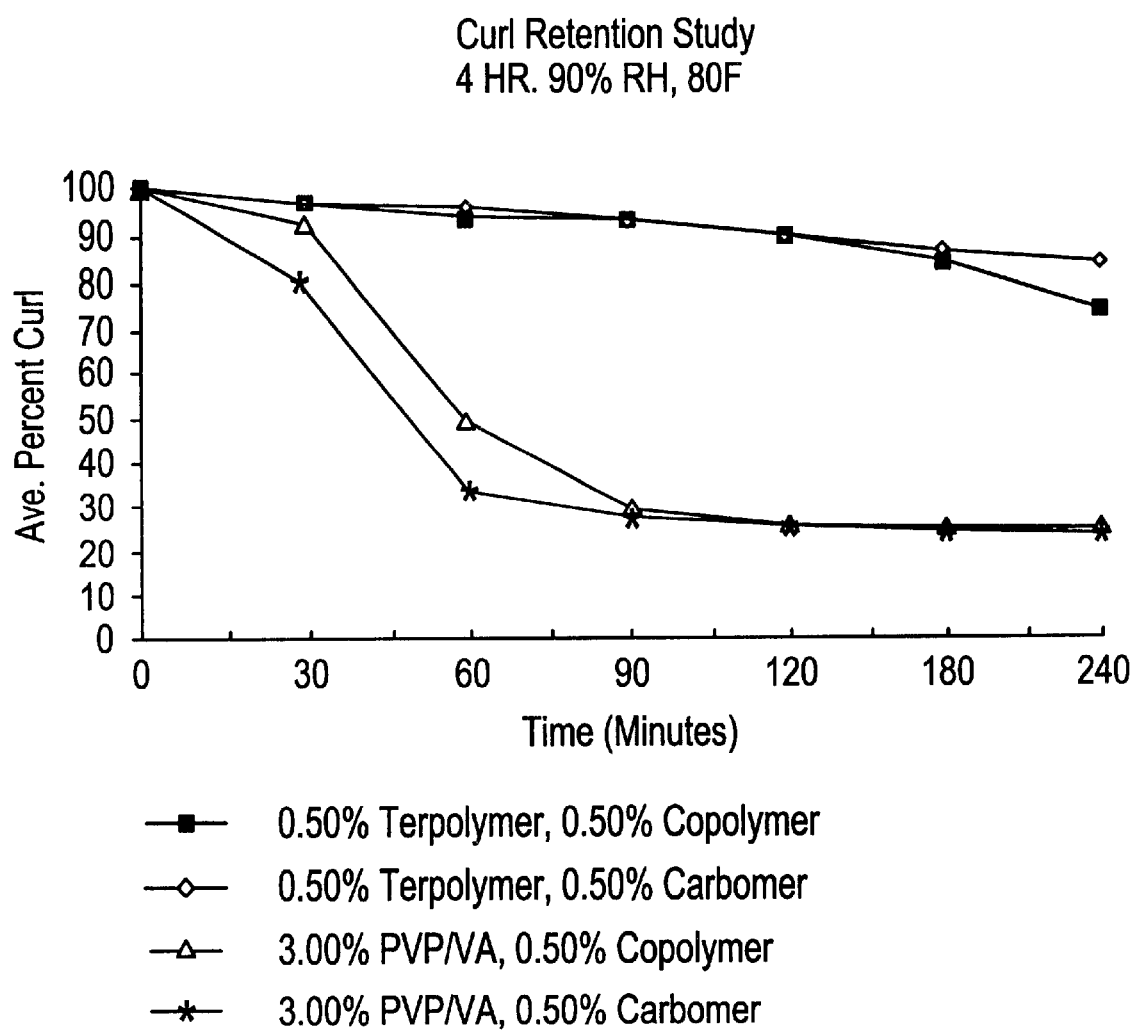

As can be seen in FIGS. 9 and 10, High Humidity Curl retention results are excellent. Excellent curl retentions are obtained at as low as 0.5% Terpolymer. Also testing in both Copolymer and Carbopol 940 produces the same excellent results; that is the gellant does not interfere with curl retention properties. These results are in distinction to formulas tested based on PVP/VA copolymer or commercial benchmarks based on PVP/VA. Despite the fact that the control formula had six times more active resin (PVP/VA at 3.0% active) the curl retention was much lower. This improved efficiency lends benefit in several respects. It allows for more cost efficient formulations. Also, performance is enhanced since having fixative properties at lower actives improves volume by not having the polymer weighing down the hair giving the appearance and feel of build up of polymer on the hair.

Hair Characteristic Testing

This test entails treating hair swatches with product and using a panel to assess the qualities on the hair in the dry state. As with Salon testing, each quality has standard criteria for evaluation so that a quantitative number can be assigned to each subjective parameter. Scores for these parameters are compiled from five panelists and assessed statistically to discern differences. Qualities under assessment are shine, stiffness, curl snap, comb drag, residue on comb and hair, curl memory, and static. Tests results indicate that the hair gel containing 0.5% Terpolymer is at parity in all hair characteristic qualities to a hair gel containing 3.0% PVP/VA.

Suspension Ability

Carbopol has been used as a stabilizing ingredient in hair care composition due to the presence of a yield value in its rheological traits. The application of this property has been utilized to perform such functions as stabilizing cream emulsions, suspending insoluble dimethicone in surfactant systems in conditioning shampoos, and suspension of insoluble particles with aesthetic/functional value in clear gel formulas. Herein it was discovered that the invention composition also has suspending properties as sown below.

Two formulas with 0.5% Terpolymer and 0.5% Copolymer was compared to a formula of 0.5% Carbopol 940 and 0.5% Terpolymer with respect to their ability to suspend particulate matter. 0.1% glitter (Fuschia 12D by Meadow Brook Inventions) was added to all formulas. The particular matter was observed to be suspended in all formulas after stability testing including elevated and depressed temperatures and exposure to sunlight.

In summary, the synergistic copolymer herein has a dual functionality, that is, to provide enhanced rheological properties and to provide fixative characteristics for hair styling, which is unexpected and advantageous for personal care formulations.

While the invention has been described with particular reference to certain embodiments thereof, it will be understood that changes and modifications may be made which are within the skill of the art. Accordingly, it is intended to be bound only by the following claims, in which:

What is claimed is:

1. A personal care gel composition having synergistic rheological and viscosity properties that provide both an aesthetic and functional gel at a low solids level comprising a blend of (a) a terpolymer of polyvinylpyrrolidone, acrylic acid and lauryl methacrylate; and (b) at least about 50% by wt. of a copolymer of acrylates and steareth-20 or beheneth-25 methacrylate.

2. A personal care gel composition according to claim 1 in which said blend is neutralized.

3. A personal care gel composition according to claim 1 wherein said blend is present in an amount of about 0.1–3 wt. % of said composition.

4. A personal care gel composition according to claim 1 which is a hair care gel product.

5. A personal care gel composition according to claim 1 in which (b) is a copolymer of acrylates and beheneth-25 methacrylate.

6. A personal care gel composition according to claim 1 wherein the wt. ratio of (a):(b) is about 25:75 at about 1% total solids.

7. A personal care gel product according to claim 1 wherein said blend is present in an amount of 1 to 3 wt. %.

8. A personal care gel product according to claim 5 wherein said blend is present in an amount of 0.75–1.25 wt. %.

9. A personal care gel composition according to claim 1 which has a viscosity of 120,000 cps at a total solids of 1% of a 50:50 blend.

10. A hair styling gel composition according to claim 1 having high humidity curl retention properties at 1% solids of a 50:50 blend.

* * * * *